(12) United States Patent  
Moser et al.

(10) Patent No.: US 8,366,788 B2  
(45) Date of Patent: Feb. 5, 2013

(54) CONTROL SYSTEM FOR A LOWER LIMB PROSTHESIS OR ORTHOSIS

(75) Inventors: David Moser, Hampshire (GB); David John Ewins, Surrey (GB)

(73) Assignee: Blatchford Products Limited, Hampshire (GB)

( * ) Notice: Subject to any disclaimer, the term of this patent is extended or adjusted under 35 U.S.C. 154(b) by 964 days.

(21) Appl. No.: 11/661,774

(22) PCT Filed: Sep. 2, 2005

(86) PCT No.: PCT/GB2005/003419  
§ 371 (c)(1),  
(2), (4) Date: Mar. 28, 2008

(87) PCT Pub. No.: WO2006/024876  
PCT Pub. Date: Mar. 9, 2006

(65) Prior Publication Data  
US 2009/0030344 A1    Jan. 29, 2009

(30) Foreign Application Priority Data  
Sep. 2, 2004  (GB) .................................. 0419480.9

(51) Int. Cl.  
*A61F 2/48* (2006.01)

(52) U.S. Cl. ........................... 623/24; 600/587; 600/595

(58) Field of Classification Search .................. 600/587, 600/595; 706/13; 623/24, 27  
See application file for complete search history.

(56) References Cited

U.S. PATENT DOCUMENTS

| | | | |
|---|---|---|---|
| 5,252,102 A * | 10/1993 | Singer et al. ..................... | 623/24 |
| 5,571,205 A | 11/1996 | James | |
| 5,888,212 A | 3/1999 | Petrofsky et al. | |
| 6,955,692 B2 | 10/2005 | Grundei | |
| 2003/0120385 A1 | 6/2003 | Etienne-Cummings et al. | |
| 2004/0049290 A1* | 3/2004 | Bedard ........................... | 623/24 |

FOREIGN PATENT DOCUMENTS

| | | |
|---|---|---|
| DE | 195 21 464 | 3/1997 |
| EP | 1 260 201 | 11/2002 |
| EP | 1 447 062 | 8/2004 |
| WO | WO 00/38599 | 7/2000 |
| WO | WO 01/72245 | 10/2001 |

OTHER PUBLICATIONS

R. Tomovic et al.; *A Finite State Approach to the Synthesis of Bioengineering Control Systems*; IEEE Transactions on Human Factors in Electronics; Jun. 1966; pp. 65-69; vol. HFE- 7; No. 2; USA XP008059109.

(Continued)

*Primary Examiner* — Max Hindenburg  
*Assistant Examiner* — Renee Danega  
(74) *Attorney, Agent, or Firm* — Alston & Bird LLP (57) ABSTRACT

In a control system for a lower limb prosthesis or orthosis, a plurality of sensors generate sensor signals representing kinematic measurements (21) relating to the movement of segments of a prosthesis or orthosis (e.g. a thigh segment and a shank segment). The sensor signals are applied in a comparison stage 22 to a plurality of comparison steps (K1, K2, K3) which produce binary outputs for feeding to a combining stage (23) in which a binary word (16) is produced, identifying a phase of limb motion. During a walking cycle, for instance, the binary word (16) changes, and the sequence of words represents a movement phase description which is used as the input for a prosthetic or orthotic movement controller.

24 Claims, 5 Drawing Sheets

OTHER PUBLICATIONS

R. Tomovic; *Multilevel Control of Mechanical Multivariable Systems as Applied to Prosthetics*; IEEE Transactions on Automatic Control; Feb. 1968; pp. 72-74; vol. AC-13; No. 1; USA; XP008059159.

R.B McGhee et al.; *An Experimental Study of a Sensor Controlled External Knee Locking System*; IEEE Transactions on Biomedical Engineering; Mar. 1978; pp. 195-199; vol. BME- 25; No. 2; USA; XP008059218.

G.A. Bekey et al.; *Robot Control by Reflex Actions*; Proceedings IEEE International Conference on Robotics and Automation; 1986; pp. 240-247; vol. 1; IEEE Comput. Soc. Press; Washington, DC; XP008059107.

R. Tomovic et al.; *The Study of Locomotion by Finite State Models*; Biological Cybernetics; 1990; pp. 271-276; vol. 63; No. 4; West Germany; XP008059124.

D.B. Popovic; *Finite State Model of Locomotion for Functional Electrical Stimulation Systems*; Progress in Brain Research; 1993; pp. 397-407; vol. 97; XP008059110.

N. Fisekovic et al.; *New Controller for Functional Electrical Stimulation Systems*; Medical Engineering & Physics Elsevier; Jul. 2001; pp. 391-399; vol. 23; No. 6; United Kingdom; XP008059167.

The International Search Report for PCT Application No. PCT/GB2005/003419; Filed Sep. 2, 2005; Date of Completion Feb. 8, 2006; Date of Mailing Feb. 17, 2006.

The International Preliminary Report on Patentability for PCT Application No. PCT/GB2005/003419; Filed Sep. 2, 2005.

\* cited by examiner

Extension Interactions

Flexion Interactions

CONTROL SYSTEM FOR A LOWER LIMB PROSTHESIS OR ORTHOSIS

This invention is in the field of biomedical engineering and the analysis of human movement, and particularly to a control system for the control of prosthetic and orthotic devices. Also presented are methods for the systematic description and analysis of lower limb motion.

Finite state models of locomotion are used to incorporate biomechanical knowledge of gait into lower limb orthotic and prosthetic control systems. The models are traditionally derived from the contributions of experts in gait biomechanics and rehabilitation technology. The resulting gait patterns are used, for example, to control the mechanical resistance of a prosthetic knee. Human gait is probably the most studied of human motions, however considerable problems remain in deriving applicable finite state models of gait. This is partly due the low number of invariant gait characteristics that can be reliably identified in real time.

Detailed measurement of gait patterns (i.e. human, animal, and artificial) is achievable through use of a well equipped biomechanical/gait laboratory. The equipment typically includes 3D optical measurement systems, force plates, plantar pressure and other motion and physiological sensing systems. The resulting measurement records can be synchronised and analysed by a central computer. The analysis may involve statistical examination of measured and calculated analogue records over a number of gait cycles. The analysis may also involve subdividing the gait cycle into discrete phases according to specific characteristics (i.e. temporal, biomechanical or invariant). Trained clinicians are able to examine the quality of gait patterns with respect to known biomechanical parameters.

The variability of gait makes analytical (numerical) approaches to gait description and control difficult. Known non-analytical methods of motor control, e.g. by selecting key features of signals from sensors, are achieved by abstracting both plant dynamics and control solutions into finite automata systems which simplifies relatively complex motor control problems and solutions. In addition, the resulting controllers are relatively insensitive to noise as control responses are only triggered by fixed sensory patterns. Consequently, the control method has been widely adopted for rehabilitation engineering applications, such as functional electrical stimulation (FES), and intelligent lower limb prosthetics and orthotics. However, such non-analytical approaches to locomotion and control modelling are achieved by simplifying gait characteristics into an applicable finite state model. Angular displacement records of both limb segments and joints are in analogue form and are therefore descriptive of individual behaviours. They cannot be used directly to model locomotion.

Tomović et al. ("The Study of Locomotion by Finite State models" Biological Cybernetics, volume 63, 1990) describes a systematic finite state approach to the modelling of locomotion. Tomović describes a method for the abstraction of locomotion phases according to locked (nonrotating), flexion and extension joint states derived from joint angular measurements. The resulting 3 state decimal coded representation (locked=0, extension=1, flexion=−1) of joint movements is not easily embedded or processed electronically. The interpretation of joint behaviour is simplistic and results in a quasi-static interpretation of dynamic joint motions. Furthermore the inclusion of the locked state which separates flexion and extension enforces a sequential interpretation of joint movements. Popović ("Finite state model of locomotion for functional electrical stimulation" Progress in Brain Research, volume 97, 1993) teaches encoding hip, knee and ankle joint angles in addition to thigh segment angles with respect to the gravity vector, according to locked, flexion and extension states as described previously. These coded inputs combined with other encoded sensory signals are processed using a preferential neural network to derive invariant phases of locomotion.

The approach to gait phase detection described by Popović is difficult to set up, complex and computationally intensive compared to the use of state machine signal processing, and is not easily embedded into a practical system. The systematic approaches to motion description of Tomović and Popović, rely on the instrumentation and characterisation of multiple joints and limbs in order to derive detailed phase descriptions of limb motion. In many prosthetic and orthotic applications it is not practically feasible to instrument multiple joints and limbs due to the encumbering nature of the resultant sensor systems. As such the potential for deriving phases of motion is diminished.

A finite state/rule based approach to the control of orthotic and prosthetic devices is described by Tomović and McGee ("A Finite State Approach to the Synthesis of Bioengineering Control systems" IEEE, Transactions on Human Factors in Electronics, Vol HFE-7, June 1966). A non-analytical means of selecting and triggering control responses according to identifiable sensory patterns. The paper describes a method of binary encoding locomotion according to sequences of predetermined joint angular positions and heel/toe contact patterns.

The application of finite state machine-based motor control is also known from Bekey and Tomović ("Robot Control by Reflex Actions", Proceedings of IEEE International Conference on Robotics and Automation, 1986). The control model is similar to the biological reflex, in which simple motor control actions are triggered by exteroceptive and proprioceptive sensory information. Replicating this type of control mechanism requires the mapping of sensory patterns to corresponding motor patterns. The mapping is represented as an "if-then" rule in a knowledge data base. The control rules are initially formulated from expert knowledge, intuition and guesswork, and are further refined by empirical testing.

According to a first aspect of the present invention, there is provided a control system as set out in claim 1 appended hereto. Preferred features of the invention include those set out in the dependent claims. The invention is also directed to a lower limb prosthesis and a lower limb orthosis including such a control system.

According to a second aspect of the invention, a method of analysing gait characteristics comprises the steps set out in claim 19 appended hereto.

The method disclosed in this specification performs finite state modelling of lower limb motion by coding limb segment interactions (CLSI). Kinematic properties, for example angular velocities of limb segments, are used to derive a binary code representative of invariant states of locomotion. The code allows, for example, knee flexion and extension phases of gait to be identified in real time in terms of the rotational interactions of the thigh and shank segments. This non-deterministic method of phase characterisation offers advantages over current gait/movement phase detection systems because, for instance, no sequences of phases are assumed to exist which otherwise would limit the analysis and control potential. The method described in this specification systematically abstracts analogue gait records into detectable invariant states. These states are defined according to a plurality of joint/segment kinematic characteristics in such a manner that a useful number of meaningful states are derived which are valid for the entire range of possible movements, and which cannot coexist in real time.

As described earlier, subdivision of the gait cycle into phases, has also proved to be of value for the synthesis of prosthetic and orthotics control systems. Sensor systems that are able to detect gait phases in real-time have provided a means of creating intelligent orthotic and prosthetic devices. It is desirable to be able to select and regulate control responses according to identifiable phases of gait. Control systems that are sensitive to the temporal characteristic of walking, are then adaptable to the users requirements improving the comfort and efficiency of gait.

The division of gait into phases has been instrumental in developing our knowledge of gait biomechanics. Description of gait in terms of sequential phases according to either temporal (early, mid, late) or functional (weight acceptance, push off) characteristics is well known. While this knowledge is useful, it is not easily embedded into microprocessor based controllers. The sophistication of current controllers is limited by a low number of detectable states, particularly during swing phase. This is partly due to the limitations of current sensor technologies as well as difficulties in sensory signal processing and interpretation.

The main difficulty associated with the application of machine-based motor control as described by Bekey and Tomović (see above) is in the defining of reliable sensory patterns which can be detected in real time. This problem is compounded further as locomotion expertise is not available in explicit form. Synthesis of finite state gait phase detection and control systems can be excessively time-consuming. Considerable human expertise tends to be required in order to identify suitable triggering sensory characteristics within analogue sensory records. Consequently the resultant system performance may depend a great deal on the skill of the system designer. Difficulties arise as sensory patterns must be unambiguous and identifiable in real time, furthermore considerable empirical testing may be required to ensure triggering sensory patterns are robust to variable walking conditions. The ultimate control objective of a lower limb orthosis or prosthesis is the control of joint motions. This can be achieved by capturing combined sensory and motor patterns in a form which is transferable to a controller. Finite state modelling of locomotion for control is mainly a machine based pattern recognition and matching activity.

In a preferred embodiment of the invention, the control system is adapted to detect and represent phases of motion that can be derived in real-time, through use of appropriate software algorithms or electronically in a manner suitable for intelligent orthotic and prosthetic control applications.

Ankle function is known to change according to walking speeds and activities (e.g. level, stair, slope walking). An automated method for the real time description and analysis of joint/limb motion forms the basis for deriving control schemes to control an orthotic or prosthetic ankle joint according to changing walking conditions.

Finite state models of locomotion derived from coded limb segment interactions (CLSI) are helpful in understanding the motor control strategies which contribute to joint angles and limb motion according to different walking conditions and may be applied to gait analysis and lower limb motor control.

The invention will now be described by way of example with reference to the drawings in which.

Lower limbs can be modelled as a pendulum chain with well-known anatomical constraints restricting the range of possible rotations. While segment motion exists in three planes, the control system described below characterises joint behaviour on the basis that the majority of limb motion exists in the sagittal plane. During walking joint positions are not fixed in space but move anteriorly and posteriorly with respect to each other at respective phases of the gait cycle. The system identifies joint flexion and extension phases using different rotational interactions. Neighbouring limb segments can rotate in combinations of either counterclockwise (CCW) or clockwise (CW) directions. The associated joint interaction between the segments can, therefore, be defined in terms of the rotational contributions of the linked segments.

Figure 1:
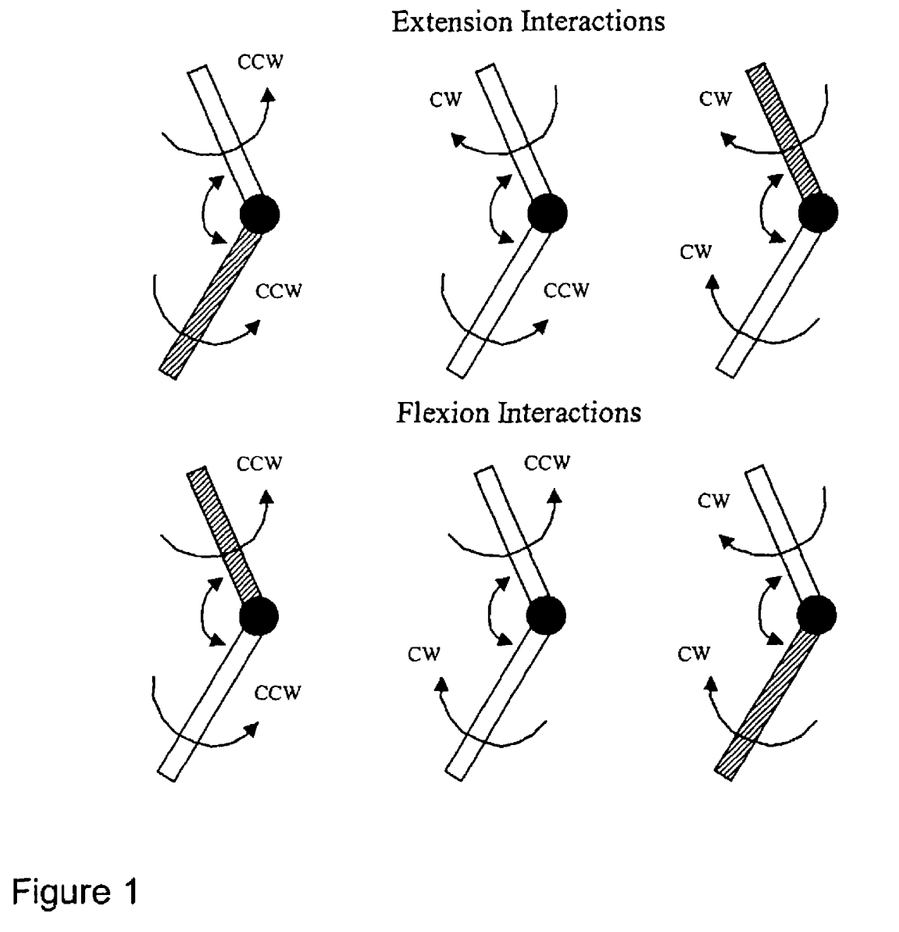
FIG. 1 is a diagram showing the rotational interaction of constituent joint segments contributing to joint behaviour (in terms of joint flexion and extension, faster rotating segments shown shaded)

Knee joint extension may occur by segments rotating in opposite directions, the thigh clockwise (CW) relative to the hip and the shank counterclockwise (CCW) relative to the knee when viewed from one side, as shown in FIG. 1. Viewed from the one side as shown in FIG. 1, the thigh rotating counterclockwise (CCW) and the shank clockwise (CW) results in joint flexion. Two invalid interactions exist in that extension cannot occur with the thigh rotating counterclockwise (CCW) and the shank rotating clockwise (CW). Similarly flexion cannot exist with the thigh rotating clockwise (CW) and the shank rotating counterclockwise (CCW). Flexion and extension states are also possible with the segments rotating in the same direction, but with one segment rotating faster than the other. The resulting six possible joint interactions are illustrated in FIG. 1.

To resolve interaction type in real time, the direction of segment rotation is determined and the faster rotating segment is identified. Analytical methods are not required. For example, the direction of segment rotation can be deduced by the sign of the angular velocity (angular velocities greater than zero being counterclockwise, less than zero being clockwise). Zero angular velocity forms a natural threshold which does not restrict data interpretation. The identification of rotational direction can be achieved from, for example, appropriate software algorithms or electronically using a system of discrete comparators. As it is only necessary to identify direction of rotation and the faster rotating segment, the signal processing can be achieved electronically in real time using a system of discrete comparators, as will be described in more detail below.

Figure 2:
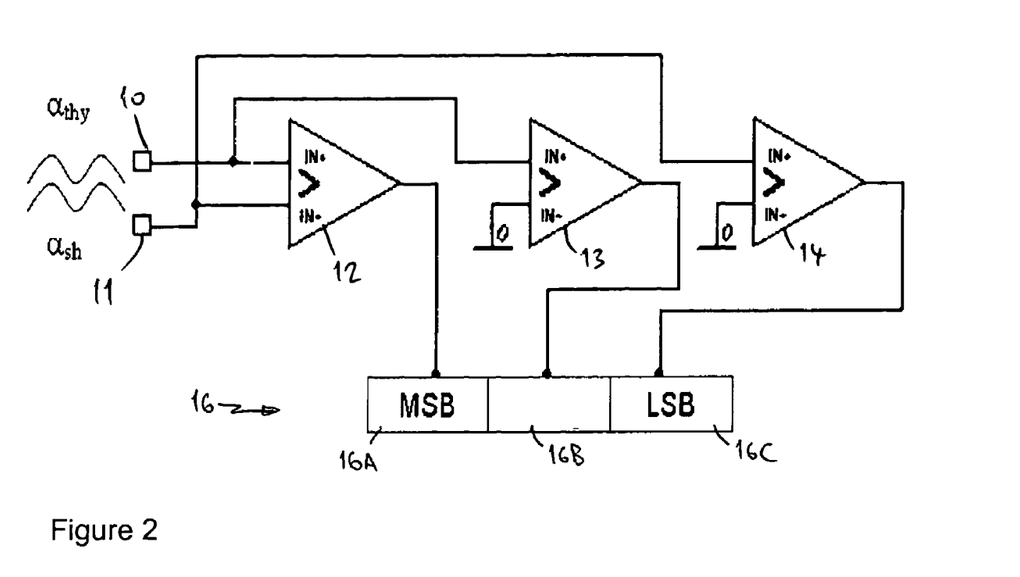
FIG. 2 is a diagram showing 3-bit interaction coding using comparators.

FIG. 2 shows how the method implemented in a circuit. $\alpha_{thy}$, $\alpha_{sh}$ are angular velocities of thigh and shank segments respectively. The angular velocities are represented by sensor signals which are fed from inputs 10, 11 of the comparator circuitry to a plurality of comparators 12, 13, 14. A first comparator compares the two angular velocity signals to produce a first output as the most significant bit (MSB) 16A of a binary word output 16. This MSB is 1 or 0 depending on whether the angular velocity of the thigh segment is greater than or less than that of the shank segment. The angular velocity of the thigh segment and shank segment are compared to zero by comparators 13 and 14 respectively. These produce intermediate and least significant bits (LSB) 16B, 16C of the binary word 16 according to whether the respective velocity is positive or negative.

In order for a controller to identify interaction in real time it is necessary to represent interactions in a form which can be easily interfaced with control hardware. This is achieved by encoding interactions into binary values, as described above. The digital output from the comparators makes this relatively straightforward. For example the six joint interactions described previously (FIG. 1) can be described using the 3-bit binary code word 16, resulting in a possible 8 states, two of which are invalid joint interactions as stated earlier. To simplify later code processing, the comparator output to the MSB 16A in this example is used for segment signal comparison. This means that for a 3-bit code any code value above or below 4 can be immediately identified as joint flexion or extension respectively. The remaining intermediate bit 16B and LSB 16C denote the directions of rotation for the thigh and shank segments respectively. An example truth table detailing, rotation states, sensory conditions and binary assignments is shown below in Table 1.

TABLE 1

Example truth table summary of possible segment interactions, sensory conditions and binary assignments. $\alpha_{thy}$, $\alpha_{sh}$ are angular velocities of thigh and shank segments respectively.

Joint Interaction

| Thigh ($\alpha_{thy}$) | Shank ($\alpha_{sh}$) | Condition | Code |
|---|---|---|---|
| | | Extension | |
| CW | CW | $\alpha_{thy} < \alpha_{sh}, \alpha_{thy} < 0, \alpha_{sh} < 0$ | 000 |
| CW | CCW | $\alpha_{thy} < \alpha_{sh}, \alpha_{thy} < 0, \alpha_{sh} > 0$ | 001 |
| CCW | CCW | $\alpha_{thy} < \alpha_{sh}, \alpha_{thy} > 0, \alpha_{sh} > 0$ | 011 |
| | | Flexion | |
| CW | CW | $\alpha_{thy} > \alpha_{sh}, \alpha_{thy} < 0, \alpha_{sh} < 0$ | 100 |
| CCW | CW | $\alpha_{thy} > \alpha_{sh}, \alpha_{thy} > 0, \alpha_{sh} < 0$ | 110 |
| CCW | CCW | $\alpha_{thy} > \alpha_{sh}, \alpha_{thy} > 0, \alpha_{sh} > 0$ | 111 |

The binary representation can be extended further by adding an extra bit to describe joint angular acceleration. However, relative joint angular velocity is a bipolar signal, and, therefore, the resulting acceleration joint state must be considered appropriately in terms of joint flexion and extension.

Figure 3:
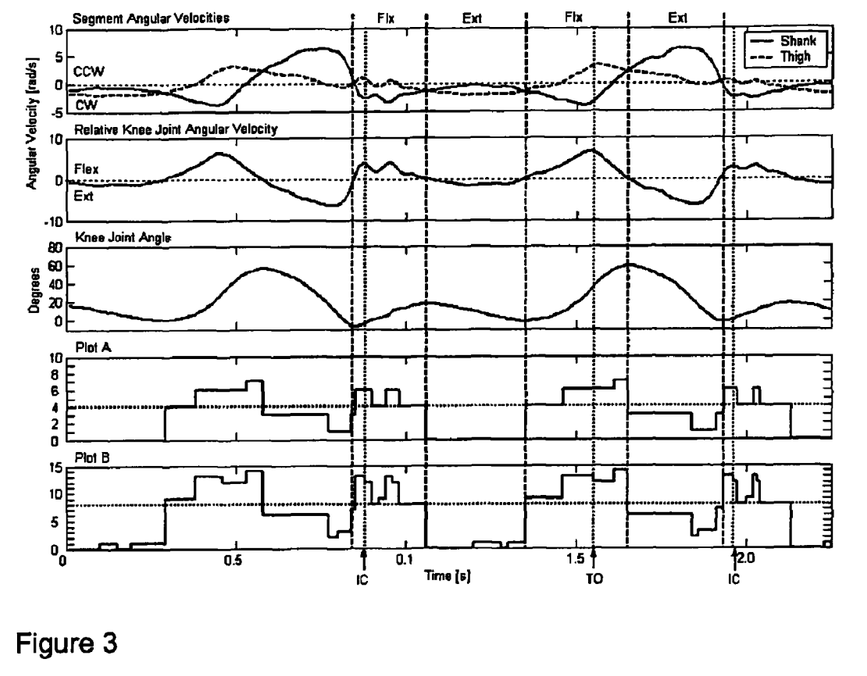
FIG. 3 comprises plots of thigh and shank angular velocities, relative knee joint angular velocity, knee angle, and binary word output values produced in first and second preferred embodiments of the invention.

The coding method applied to a normative data record is presented in FIG. 3. The method presented is implemented without assuming the existence of predefined ranges or states within the analogue data record. The interpretation of gait is not specific to any one type of activity. This method could also be used for the analysis of other walking motions. The coding strategy presented compares favourably with previous finite state modelling strategies, in that a greater number of states has been abstracted, and the interpretation of gait is not restricted by presumptions. The coding strategy accounts for all possible thigh and shank interactions and is derived directly from gait kinematics. The possibility therefore exists to use the method in more general gait analysis applications.

Adopting a non-analytical approach to control makes numerical analysis of data redundant; however, characterisation into states is still required. Human gait is a dynamic motion. It is not inappropriate, therefore, to describe it in terms of velocity and acceleration. The CLSI method results in the simultaneous invariant representation of multiple segment rotations. The method is descriptive of the motor strategies/synergies used to achieve the joint angles which orientate the limb in space. The code transitions are directly descriptive of kinematic changes and, therefore, have some value in the planning of motion executions and the synthesis of motor control rules. CLSI strategies as presented are capable of converting analogue data records into digital codes in real time. Knowledge pertaining to the significance of the code states and sequences are easily built into control algorithms. The controller identifies perturbations and predicts gait phases from a built in knowledge base of code sequences and transition timings.

Figure 4:
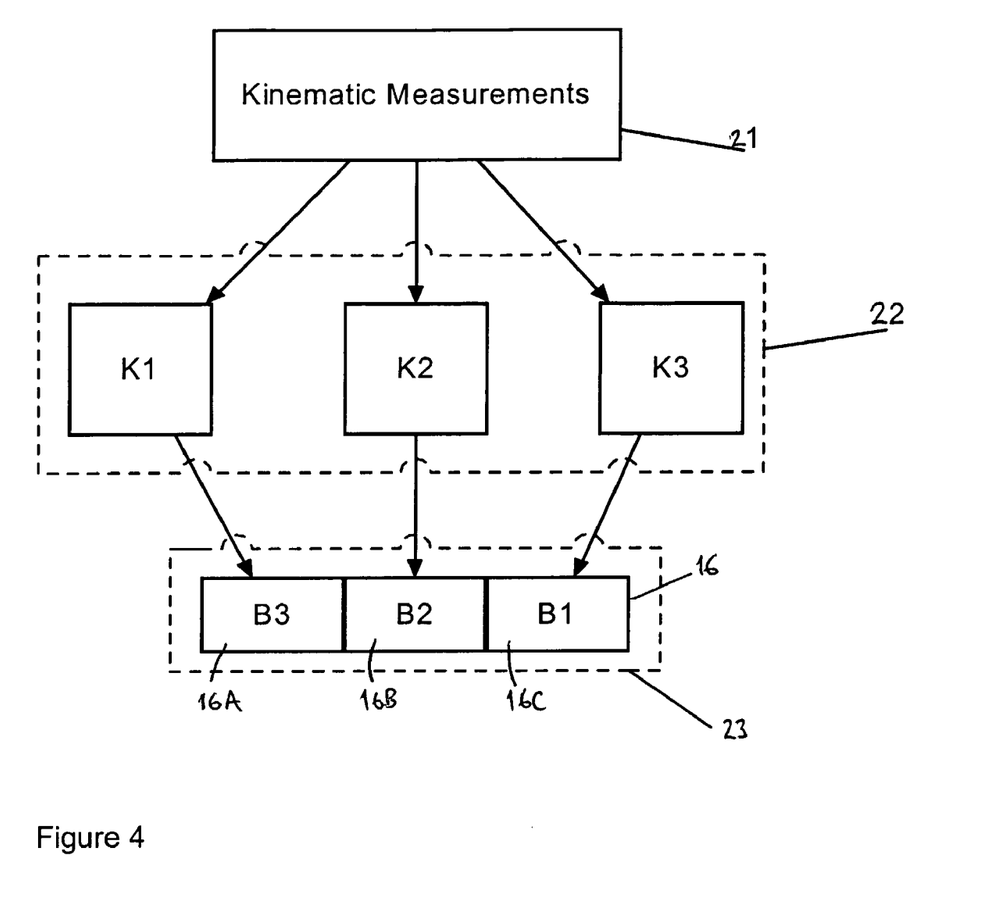
FIG. 4 is a flow diagram of a signal processing procedure used in a control system in accordance with the present invention.

Referring to the flow diagram of FIG. 4, in an exemplary process performed by the preferred control system in accordance with the invention, kinematic measurements are firstly made 21 in order to determine directly or derive joint and/or segment angular records. These records may include angular displacement, angular velocity and angular acceleration in all three planes, although the description herein is limited to sagittal motion. The kinematic measurements 21 may also include sensor signals from which it is possible to determine direction of segment rotation. A plurality of sensory measurement systems may be used which may include and is not limited to gyroscopes, accelerometers, tilt sensors and optoelectronic camera system, or a combination of these. Direct measurement of the motion of a given limb segment is made by means of such a sensor mounted on the segment itself. Derived measurements can be obtained from a sensor on another limb segment. The kinematic measurements 21 are processed and categorised by a binary (2-state) processing phase 22. The binary processing phase 22 consists of a plurality of kinematic parameter comparators K1, K2, K3 arranged in parallel. Additional kinematic parameter comparators can be added to the array of existing kinematic parameter comparators K1, K2, K3 indefinitely, to incorporate kinematic measurements from any other part of the body, e.g. ankle, hip, trunk, etc. Comparative states are defined in such a fashion that at least one of each of the individual comparator parameter states must exist at any time. The kinematic parameter state conditions are defined unambiguously so that states cannot coexist. The kinematic parameters examined are not limited and may include any two descriptive states for example:

Joint flexion/Joint extension
Joint abduction/Joint adduction
Joint external rotation/Joint internal rotation
Joint angular-acceleration/Joint angular-deceleration (i.e., sagittal, transverse and frontal planes)
Clockwise segment direction/Counter-clockwise segment direction (i.e. in 3 planes)
Single measurement threshold value—above/below Each of the kinematic parameter comparators, K1, K2 and K3 are non-analytical processing element and the comparison is analogous to determining the truth of a sensor (kinematic property) condition. At the comparison stage 22 the kinematic parameter comparators K1, K2, K3 may operate synchronously or asynchronously and are able to determine kinematical parameters by, for example, comparing the kinematic measurements 21 with predefined threshold values (e.g. zero crossings) or with other sensory measurements. The kinematic parameter comparators 22 are discrete and are able to operate independently from each other. The kinematic parameter output states are given an arbitrary binary assignment B1, B2 and B3 in a combination stage 23 where they are combined to produce a binary word 16. It will be understood by a person skilled in the art that the binary word 16 identifies a unique set of states, otherwise termed 'phase of motion'. In the present example there are six states, as shown, although there would be more if further kinematical parameters are employed.

The process described with reference to FIG. 4 is repeated at intervals of for example 1 millisecond to produce a continuous gait analysis, which may be termed a movement phase description. Referring again to FIG. 3, such a movement phase description can be seen as plot A, which is derived from the Segment Angular Velocities as input data also shown in FIG. 3. In this example, joint flexion/extension is derived from both of the constituent segment rotational directions and magnitudes.

This non-analytical method of motor control is computationally less demanding than other classical control methods, however identifying gait characteristics is still required. Human gait appears as repeating patterns of oscillatory trajectories. It is therefore appropriate to describe gait patterns in terms of angular velocity and acceleration. The CLSI code transitions are detectable in real time, directly descriptive of kinematical changes and may be used for planning motion executions. The CLSI method results in a binary code which can be easily interfaced with ancillary control hardware. The controller is able to identify perturbations from a built-in knowledge of CLSI code sequences and transition timings, which can be used in the synthesis of prosthetic and orthotic control processes.

Further phases of joint motion may be categorised according to the following parameters:
  Directions of rotation of both constituent joint segments
  Joint flexion/extension+1 constituent segment direction of rotation
  Directions of rotation of both constituent joint segments+joint angular acceleration/deceleration
  Joint flexion/extension+1 constituent segment direction of rotation+joint angular acceleration/deceleration
  Joint flexion/extension+both constituent segment directions of rotation+joint angular acceleration/deceleration.

A resulting (4-bit) movement phase description of this embodiment is illustrated in FIG. 3 as plot B.

Additional Kinematic parameters may be included in a single joint description, these may include, for example:
  Joint flexion/extension.
  Joint abduction/joint adduction.
  Joint external rotation/joint internal rotation.
  Joint angular acceleration/deceleration. (i.e. in sagittal, transverse, frontal planes)
  Segment rotational directions clockwise/counter clockwise (i.e. in sagittal, transverse, frontal planes).
  Segment angular acceleration/deceleration (i.e. in sagittal, transverse, frontal planes).

Figure 5:
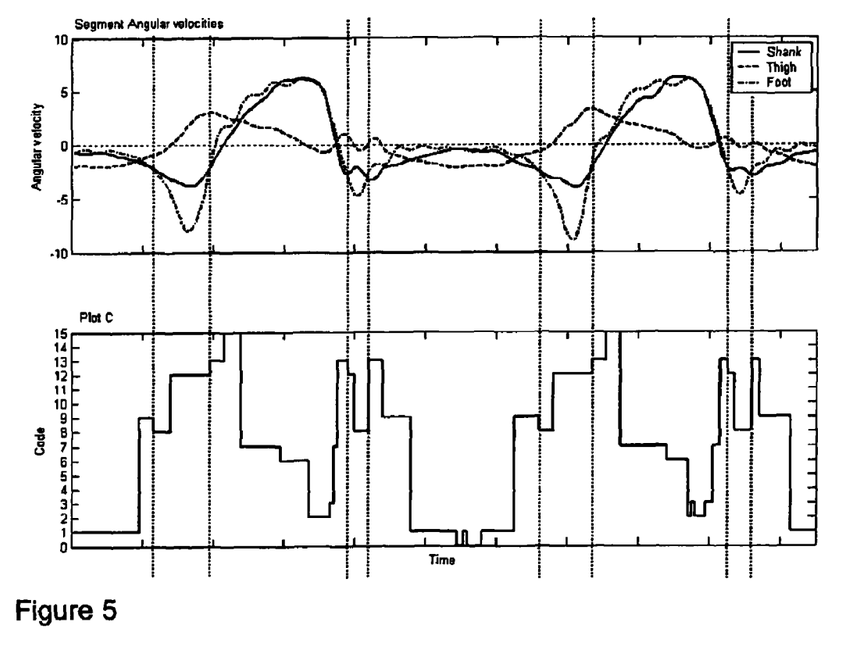
FIG. 5 comprises plots of thigh, shank and foot angular velocities, and binary word output values produced in a third preferred embodiment of the invention (according to knee flexion/extension, ankle plantarflexion/dorsiflexion and thigh and shank segment directions of rotation)

A resulting movement phase description is illustrated in FIG. 5. The description appears as plot C which includes phases defined according to knee flexion/extension, ankle plantarflexion/dorsiflexion and thigh and shank directions of rotation, as will be seen by comparing plot C with the angular velocities of the shank, thigh and foot plotted immediately above in FIG. 5.

To those skilled in the art it should be apparent that the kinematic parameters processed by the comparators K1, K2, K3 are weighted according to the positions of their respective output bits B1, B2, B3 within the binary word 16. The position a particular parameter bit takes within the word is arbitrary and is not restricted to any format, although certain arrangements may simplify later code processing. While analogue sensor signals are supplied to the kinematic parameter comparators 22 a continuous binary description of motion is produced in real-time. As the binary code changes according to changing movements, it is possible to identify any changes in the kinematic parameters either from the position of changing bits or from changes in the numerical value of the binary description word in the movement phase description. The parallel state processing architecture described above with reference to FIG. 4 offers a systematic means of characterising movement according to a plurality of kinematic parameters. This has an advantage over the majority of previously disclosed phase description systems, where deterministic sequential state machines are used to detect assumed phases sequences. An entirely sequential approach to gait phase description and detection limits analysis and control potential.

Figure 6:
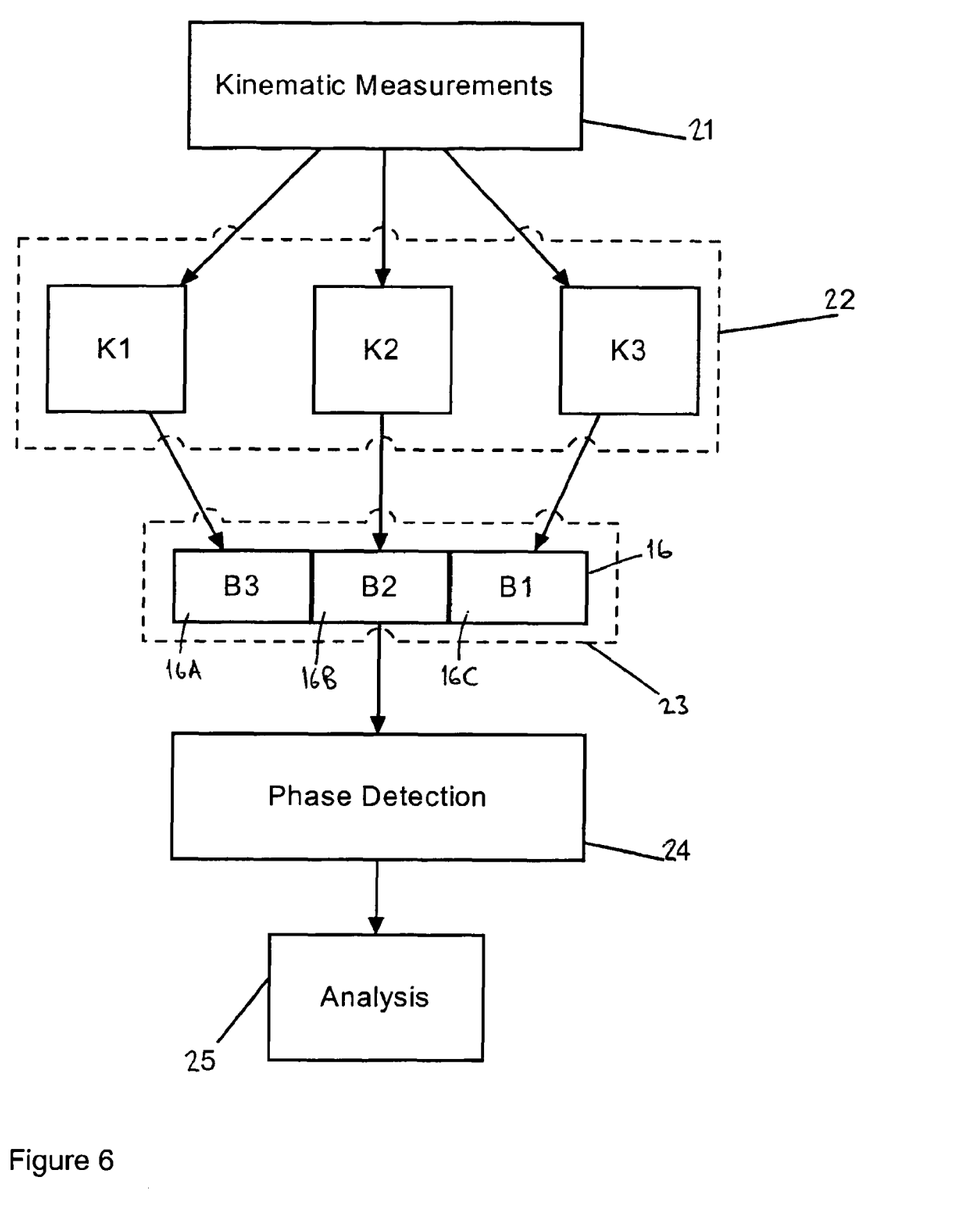
FIG. 6 is a flow diagram of a signal processing and analysis procedure used in an alternative control system in accordance with the invention.

A further process which may be used in a control system in accordance with the invention is now described with reference to FIG. 6. In this case the measurement, comparison and word formation steps are performed as described with reference to FIG. 4. The binary coded movement description represented by the changing binary word 16 provides a framework for a gait phase detection step 24 and a further analysis step 25. In these steps, state machines are used to identify singular binary code transitions or particular sequences of coded phases. The kinematics and kinetics of walking are known to change according to varying walking activities and speeds. In many lower limb motor control applications it is desirable to be able to able to detect changing kinematic and/or kinetic parameters according to changing walking speeds and activities. Software algorithms may be used to automate further levels of analysis which may include examining kinematic and/or kinetic parameters at code transitions and/or over selected phases. These parameters (i.e. in 3 planes) may or may not be analysed 25 with respect to code transition timings and may include for example and are not limited to:
At Code Transitions:
  Joint angles—angle, angular velocity, angular acceleration
  Segment—angle, angular velocity, angular acceleration
  Segment Tangential/radial—acceleration, velocity, displacement
  Segment/joint bending moment
  Plantar pressure/force
  Joint segment mechanical energy (kinetic translational and rotational, potential and elastic)
Over Selected Phase/s
  Electromyography (EMG) muscle activity
Over Selected Phase/s, Differences in (Calculated Increase/Decrease):
  Joint angles—angle, angular velocity, angular acceleration
  Segment—angle, angular velocity, angular acceleration
  Segment tangential/radial—acceleration, velocity, displacement
  Segment/joint bending moment
  Plantar pressure/force
  Joint segment mechanical energy (kinetic translational and rotational, potential and elastic)
Over Selected Phase/s, Integrals of:
  Joint—angle, angular velocity, angular acceleration
  Segment—angle, angular velocity, angular acceleration
  Segment tangential/radial—acceleration, velocity, displacement
  Segment/joint bending moment
  Plantar pressure/force The processes described above are embedded into microprocessor control architecture and software. Limb or joint motion is modelled at different walking speeds and activities (level, slope, stair, cycling, running, etc.). These models form the basis of a 'Biomechanical knowledge' that is embedded into the control system. The embedded models may include code sequences, transition timing, and/or other measured or derived parameters, relating to codes transition/s and/or phase/s as described in the analysis step 25 of the process shown in FIG. 5. These models for comparison are used in the control system in order to adjust control responses according to changing walking speeds and activities. The code transitions themselves are used directly to regulate the execution of control responses.

To those skilled in the art it may be apparent that changing code sequence patterns and/or associated transition/phase derived parameters may form the basis of defining fuzzy sets/phases. Fuzzy logic systems provide a means of dealing with the uncertainty and imprecision of sensory measurement and are analogous to human reasoning. Fuzzy sets/phases can be mapped to a fuzzy set of control parameters using a set of rules. Incoming sensory measurements and/or derived parameters can be compared to embedded fuzzy models and a degree of fuzzy set/phase/parameter membership calculated. A rule-based mapping algorithm is used to map the fuzzy input to a fuzzy output/control parameter. Such an approach may provide a means of adjusting control parameters and responses.

The skilled person will also be aware of the relevance of the invention in the field of computer animation and gaming, as well as its application to the control of robotic and bionic machines.

The invention claimed is:

1. A control system for a lower limb prosthesis or orthosis, comprising:
   a plurality of sensors for generating electrical sensor signals representative of kinematic parameters which relate to the motion of upper and lower limb segments of the prosthesis or orthosis, said sensor signals indicating at least one of limb segment velocity and limb segment acceleration for each said limb segment,
   an electronic processing circuit including a comparison stage for comparing the kinematic parameters of said limb segments with each other and outputting corresponding binary state values, and
   a combination stage in which the binary state values are combined to produce a binary word representing a phase of motion.

2. A control system according to claim 1, wherein the comparison and combination stages are arranged to perform comparing and combining operations repeatedly to produce a sequence of the said binary words which sequence represents a limb movement description comprising a series of unique gait phases each represented by a respective said binary word.

3. A control system according to claim 1, wherein the sensors and the processing circuit are arranged to produce binary state values for at least two kinematic parameters each relating to the motion of a respective limb segment of the prosthesis or orthosis.

4. A control system according to claim 3, wherein the kinematic parameters include a first parameter representative of the motion of a thigh segment and a second parameter representative of the motion of a shank segment.

5. A control system according to claim 4, wherein the kinematic parameters include a third parameter representative of the motion of a foot segment.

6. A control system according to claim 1, wherein the comparison stage is arranged to compare a first kinematic parameter with a second kinematic parameter to produce a first binary state value, and to compare at least one of the kinematic parameters with a zero reference value to produce a second binary state value indicative of the polarity of the parameter.

7. A control system according to claim 6, wherein the first and second kinematic parameters are angular velocities and the first binary state value is indicative of joint flexion and extension.

8. A control system according to claim 6, wherein the first binary state value forms the most significant bit (MSB) of the binary word.

9. A control system according to claim 1, wherein the comparison stage is arranged to compare a first kinematic parameter with a second kinematic parameter to produce a first parameter state value, to compare the first kinematic parameter with a predefined threshold value to produce a second parameter state value, and to compare the second kinematic parameter with a predefined threshold value to produce a third parameter state value, the combination stage being arranged to form the binary word from the first, second and third parameter state values, the word having at least three bits.

10. A control system according to claim 9, arranged to measure a third said kinematic parameter, and wherein the comparison stage is arranged to compare the third kinematic parameter with a threshold value to produce a fourth parameter state value, the combining stage being arranged to combine the fourth parameter state value with the first to third parameter state values to form a binary word of at least four bits.

11. A lower limb prosthesis including a controller for controlling joint motions, and a control system according to claim 1, wherein the controller is coupled to the control system to receive said binary or signal words and to generate control responses thereto.

12. A lower limb prosthesis including a control system according to claim 1, the control system further including a knowledge base representing models of different limb activities and being arranged to use the models for comparison and to adjust control responses according to changing walking speeds and/or activities.

13. A prosthesis according to claim 12, wherein the models each comprise a respective sequence of the said binary words.

14. A lower limb orthosis including a controller for controlling joint motions, and a control system according to claim 1, wherein the controller is coupled to the control system to receive said binary words and to generate control responses thereto.

15. A lower limb orthosis including a control system according to claim 1, the control system further including a knowledge base representing models of different limb activities and being arranged to use the models for comparison and to adjust control responses according to changing walking speeds and/or activities.

16. An orthosis according to claim 15, wherein the models each comprise a respective sequence of the said binary words.

17. A control system for a lower limb prosthesis or orthosis comprising;
   a plurality of sensors adapted and arranged to produce sensor outputs representative of kinematic parameters which relate to the motion of upper and lower limb segments of the prosthesis or orthosis, said sensor signals indicating the angular velocities or angular accelerations of each of said limb segments of the prosthesis or orthosis, and an electronic processing circuit arranged to perform a non-deterministic process of gait phase characterization based on said kinematic parameters of said limb segments to produce a digital movement description as a series of signal words representing successive movement phases which are characterised according to a common set of said kinematic parameters.

18. A control system according to claim 17, wherein each signal word represents a unique gait phase.

19. A lower limb prosthesis including a control system according to claim 17, the control system further including a knowledge base representing models of different limb activities and being arranged to use the models for comparison and to adjust control responses according to changing walking speeds and/or activities.

20. A lower limb orthosis including a control system according to claim 17, the control system further including a knowledge base representing models of different limb activities and being arranged to use the models for comparison and to adjust control responses according to changing walking speeds and/or activities.

21. A method of analysing gait characteristics comprising the steps of:

receiving kinematic measurement data, said kinematic measurement data comprising kinematic parameters representing the motion of relatively moving upper and lower limb segments of a limb, the kinematic parameters being limb segment velocity and/or limb segment acceleration for each said limb segment, comparing said kinematic parameters of said limb segments with each other and outputting kinematic parameter state values, each said parameter state value being one of two values in dependence on the result of said comparison, and combining the parameter state values to produce a binary word, said binary word representing a unique gait phase.

22. A method of analysing gait as claimed in claim 21 wherein, a first kinematic parameter is compared to a second kinematic parameter to produce a first parameter state value, said first kinematic parameter is compared to a predefined threshold value to produce a second parameter state value, said second kinematic parameter is compared to a predefined threshold value to produce a third parameter state value and wherein the binary word is formed from said first, second and third parameter state values.

23. A method of analysing gait as claimed in claim 22 wherein, a third kinematic parameter is measured and compared to a threshold value to produce a fourth parameter state value and said fourth parameter state value is appended to said binary word.

24. A method of analyzing gait according to claim 21, wherein the kinematic parameters include the angular velocities or accelerations of thigh and shank segments of a lower limb prosthesis.

* * * * *

UNITED STATES PATENT AND TRADEMARK OFFICE
CERTIFICATE OF CORRECTION

PATENT NO.         : 8,366,788 B2
APPLICATION NO.    : 11/661774
DATED              : February 5, 2013
INVENTOR(S)        : David Moser et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1083 days.

Signed and Sealed this
Third Day of March, 2015

Michelle K. Lee
*Deputy Director of the United States Patent and Trademark Office*

UNITED STATES PATENT AND TRADEMARK OFFICE
CERTIFICATE OF CORRECTION

PATENT NO. : 8,366,788 B2  Page 1 of 1
APPLICATION NO. : 11/661774
DATED : February 5, 2013
INVENTOR(S) : Moser et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1474 days.

Signed and Sealed this

First Day of September, 2015

Michelle K. Lee
*Director of the United States Patent and Trademark Office*